United States Patent
Dean et al.

(10) Patent No.: US 6,316,441 B1
(45) Date of Patent: Nov. 13, 2001

(54) BRINZOLAMIDE AND BRIMONIDINE FOR TREATING GLAUCOMA

(75) Inventors: Thomas R. Dean, Weatherford; Louis Desantis, Jr., Fort Worth; Billie M. York, Conroe, all of TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/832,998

(22) Filed: Apr. 11, 2001

Related U.S. Application Data

(63) Continuation of application No. 09/601,634, filed on Aug. 4, 2000.
(60) Provisional application No. 60/112,750, filed on Dec. 17, 1995.

(51) Int. Cl.[7] .................................................. A61K 31/535
(52) U.S. Cl. ....................... 514/222.8; 514/363; 514/913
(58) Field of Search ................................ 514/363, 222.8, 514/913

(56) References Cited

U.S. PATENT DOCUMENTS

| | | | |
|---|---|---|---|
| 3,890,319 | 6/1975 | Danielewicz et al. | 260/250 |
| 5,378,703 | 1/1995 | Dean et al. | 514/222.8 |
| 5,756,503 | 5/1998 | Burke et al. | 514/249 |
| 5,948,801 | 9/1999 | Doshi et al. | 514/363 |

FOREIGN PATENT DOCUMENTS

| | | |
|---|---|---|
| 96/37203 | 11/1996 | (WO) . |
| 97/01339 | 1/1997 | (WO) . |

OTHER PUBLICATIONS

Grunwald, et al., "Effects of dorzolamide hydrochloride 2% on the retinal circulation" *ACTA Ophthalmologic*, vol. 75:236–238, 1997.

Pillunat, et al., "Effect of dorzolimide on optic nerve head blood flow," *Investigavtive Ophthalmology & Visual Science*, vol. 38(4):S776, Abstract 3592, Mar. 15, 1997.

Shipman et al., "Effect of Trusopt on IOP and choroidal blood flow in the rabbit," *Invest Ophthal & Vis Sci*, vol. 38(4):S783, Abstract 3633, Mar. 15, 1997.

Koller et al., "Effect of dorzolamide on peripapillary retinal blood flow," *Investigative Ophthalmology & Visual Science*, vol. 38(4):S276, Abstract 1284, Mar. 15, 1997.

Harris et al., "Effects of topical dorzolamide on retinal and retrobulbar hemodynamics," *ACTA Ophthalmologica*, vol. 74:569–572, 1996.

Sugrue et al., "The preclinical pharmacology of dorzolamide hydrochloride, a topical carbonic anhydrase Inhibitor," *Journal of Ocular Pharmacology and Therapeutics*, vol. 12(3):363–376, 1996.

Sponsel et al., "Does dorzolamide 2% protect against hyperventilation–induced depression of perimacular Circulation?" *Invest Ophthal & Vis Sci.*, vol. 37(3):S269, Abstract 1238, Feb. 15, 1996.

Sponsel et al., "Dorzolamide affects the relationship between retinal microcirculation and visual function HRF Findings," *Invest Ophthal & Vis Sci.*, vol. 38(4):S439, Abstract 2078, Mar. 15, 1997.

*Primary Examiner*—Zohreh Fay
(74) *Attorney, Agent, or Firm*—Sally S. Yeager

(57) ABSTRACT

Methods and compositions for treating ocular conditions which find their etiology in compromised ocular blood flow with brinzolamide and brimonidine are disclosed.

2 Claims, No Drawings

BRINZOLAMIDE AND BRIMONIDINE FOR TREATING GLAUCOMA

This application is a continuation of U.S. Ser. No. 09/601,634, filed Aug. 4, 2000, which derives priority from U.S. Ser. No. 09/928,987, filed Dec. 7, 1999, which claims priority from U.S. Pat. No. 60/112,750, filed Dec. 17, 1998.

This invention relates to the treatment of ocular diseases and conditions which find their etiology in compromised blood flow with novel formulations of brinzolamide combined with brimonidine tartrate and the use of brinzolamide and brimonidine tartrate administered separately.

BACKGROUND OF THE INVENTION

Brinzolamide R-(+)-4ethylamino-3,4-dihydro-2-(3-methoxy)propyl-2H thieno[3,2,e]1,2 thiazene-6-sulfonamide-1,1 dioxide) is a carbonic anhydrase inhibitor disclosed in U.S. Pat. No. 5,378,703 and sold in a topical ophthalmic formulation (Azopt™) for lowering elevated intra-ocular pressure (IOP) in patients with open-angle glaucoma or ocular hypertension (OHT) (Alcon Laboratories, Inc., Fort Worth, Tex.).

Brimonidine tartrate ((5-bromo-6-2-imidzolidisnylideneamino) quinozoline L-tartrate) hereinafter "brimonidine" is a relatively selective alpha-2-adrenergic agonist sold in a topical ophthalmic formulation (Alphagan™) for lowering elevated IOP in patients with open angle-glaucoma or ocular hyp e r tension (Allergan, Inc., Irvine, Calif.).

U.S. Pat. No. 3,890,319 discloses a class of compounds, including brimonidine, and their usefulness as antihypertensive agents. Certain co mpounds in the group have also been disclosed for treating physical pain, anaesthetizing[] the central nervous system, to constrict blood vessels, treat ischemia, decongest nasal passages, effect reduction of one or more effects of an inflammatory disorder to increase retinal blood flow, and effect an altration in the rate of fluid transport in the gastrointestinal tract, see U.S. Pat. No. 5,756,503 (Column 1, lines 16–22). WO 97/01339 discloses the use of brimonidine to protect the optic nerve and the retina from "noxious provocations," see page 1, first paragraph.

Oral and i.v. administration of the CAIs, acetazolamide and methazolamide, are known to increase both ocular and cerebral blood flow. The dosages used to achieve meaningful results are relatively high and is due to a number of factors. These compounds have relatively low affinity for carbonic anhydrase in as measured by their Ki (disassociation constant) values and are only modest inhibitors of the enzyme as measured by their $IC_{50}$ values. They have low distribution coefficients (octanol/water determined at pH 7.4) which is a measure of their lipophilicity. This low lipophilicity limits their ability to cross the blood retinal barrier. Finally, these compounds have relatively short half-lives in whole blood. This relatively rapid elimination rate limits their ability to redistribute into the back of the eye and maintain adequate drug concentrations.

The preclinical and clinical data for the effect of topically dosed CAIs, in particular dorzolamide, on ocular blood flow are conflicting. Gruenwald, et al., Acta Ophthalmologica, 75:236–238 (1997) disclosed that the use of dorzolamide has no effect on retinal vein blood flow in normal volunteers. Pillunat, et al., ARVO abstract, Investigative Ophthalmology & Visual Sciences, Vol. 38, No. 4 (Mar. 15, 1997) showed that topical dorzolamide did not alter optic nerve head blood flow in healthy subjects. Shipman, et al., ARVO abstract, Investigative Ophthalmology & Visual Sciences, Vol. 38, No. 4 (Mar. 15, 1997) found that dorzolamide did not alter the choroidal pressure flow relationships. Koller, et al., ARVO abstract, Investigative Ophthalmology & Visual Sciences, Vol. 38, No.4 (Mar. 15, 1997) showed that topical dorzolamide did not change peripapillary blood flow. A study by Harris, et al., Acta Ophthalmologica, 74:4896 (1996) said dorzolamide accelerated blood velocity in the retina and superficial optic nerve head; and another study by Sugrue, et al. J. Ocular Pharm., 12 (3) 363–376 (1996) teaches that topical dorzolamide does not decrease blood flow to the iris, ciliary processes, optic nerve, or retina in rabbits. Sponsel has presented a few studies which suggest that topical dorzolamide has a positive effect on ocular blood flow. See ARVO abstracts, Investigative Ophthalmology & Visual Sciences, Vol. 37, No. 3 (Feb. 15, 1996) and Vol. 38, No. 4 (Mar. 15, 1997). Healthy subjects treated with dorzolamide exhibited accelerated artereovenous passage time and an increase in optic nerve head velocity is described in WO 96/37203. The publication further discloses the use of topical carbonic anhydrase inhibitors (CAIs) to increase retinal and optic nerve head blood velocity. Brinzolamide is not disclosed in any of these references.

SUMMARY OF THE INVENTION

This invention is directed to the use of brinzolamide in combination with brimonidine to treat ocular diseases which have their etiology in compromised blood flow. These diseases include, but are not limited to glaucoma, occlusion conditions, diabetic retinopathy, and ocular neovascularization. These agents can be used either alone, in separate compositions dosed within 5 to 10 min of each other, or together in a single formulation.

DESCRIPTION OF PREFERRED EMBODIMENTS

Brimonidine is a potent and relatively selective $\alpha_2$ agonist which has been shown to effectively lower IOP in rabbits, monkeys and man. Upon topical ocular administration brimonidine causes vasoconstriction in scleral vessels. However, brimonidine does not appear to be a vasoconstrictor in vessels in the back of the eye. While brimonidine is a relatively safe compound it has been shown to cause the side effects of sedation and ocular hyperemia in an allergic like reaction in some patients. These side effects are thought to be due to the relatively high concentration of the drug administered topically. The sedation like side effects are believed to be caused by the drug crossing the blood brain barrier and triggering the sedative effects. The mechanism by which brimonidine causes hyperemia is not well understood. It is likely that the frequent instillation of relatively high drug concentrations causes this side effect. Thus, lowering the overall dose of brimonidine while maintaining IOP control would be advantageous.

Combinations of brimonidine and brinzolamide represent a novel approach to producing potent and long lasting IOP lowering medications with fewer side-effects than observed when these are administered alone.

When two separate formulations of brinzolamide and brimonidine are used, the preferred administration sequence is brimonidine first and brinzolamide second. In this case, brimonidine serves to constrict ocular vessels and thereby reducing the flux of blood through the anterior portion of the eye. When brinzolamide is administered the reduced circulation in the eye should result in an increase in the bioavailability of the CAI. Overall this sequence is expected to result in an increase in efficacy and duration of actions thereby reducing the frequency of administration (i.e., from tid to bid). This would also result in improved patient compliance.

When a single formulation of both agents is used the above advantages are believed to apply. In addition, the novel compositions contemplated have relatively high viscosity and are expected to increase the retention of brimonidine in the cul-de-sac of the eye. The net impact allows for lowering the dose of brimonidine.

It is well established that blood flow is impaired in glaucoma; many researchers think there is a direct relationship between insufficient blood flow and neural damage. Thus, improving blood flow should decrease the rate of damage. Clearly, any vascular occlusive event in the eye leads to damage to the region with restricted blood flow; improving blood flow in this region or in close-by tissue should minimize the severity of this damage. The standard treatment for advanced diabetic retinopathy is retinal photocoagulation; this is thought to be effective by decreasing oxygen demand and thus decreasing the hypoxic signal released by the oxygen-starved tissue that leads to angiogenesis. Treatment that improves oxygen supply by improving ocular blood flow as proposed here would be preferable to this tissue destruction and should lead to the same benefit. Neovascularization of the retinal, choroidal, or iridial tissues arises by the action of angiogenic substance(s). Generally, these angiogenic substances are produced in ocular tissue which is suffering from hypoxia. Thus, it is believed that enhancing blood flow in these tissues will effectively prevent or stop neovascularization by alleviating the hypoxia.

Brinzolamide is a carbonic anhydrase inhibitor which has been found to be effective in lowering the elevated intraocular pressure associated with ocular hypertension and glaucoma. The distribution coefficient, $IC_{50}$ and Ki values for brinzolamide are 6.56, 3.19 nM and 0.13 nM respectively. Further studies discussed in the examples show that it penetrates to the back of the eye following topical ocular delivery and is also effective in increasing blood flow in ocular tissues including the optic nerve head. Ocular diseases and conditions which find their etiology in compromised blood flow can be treated with brinzolamide. These diseases and conditions include glaucoma including but not limited to primary open angle glaucoma (POAG) and normal tension glaucoma also known as low tension glaucoma or angle closure glaucoma, occlusion conditions, such as, branch vein occlusion and retinal artery or vein occlusion, diabetic retinopathy, and retinal or iris neovascularization from any cause.

The distribution coefficients for other well known CAIs, methazolamide, acetazolamide and dorzolamide, are 0.64, 0.23, and 1.72 respectively. The $IC_{50}$ values (determined against human carbonic anhydrase II) are 12.5 nM, 9.04 nM, and 3.74 nM respectively. The Ki values are 29.3 nM, 33.8 nM, and 0.51 nM respectively. Dorzolamide is significantly more potent than either acetazolamide or methazolamide as measured by Ki and $IC_{50}$ and is only slightly, ~2x, more lipophilic as measured by its distribution coefficient. Thus, it is not expected to efficiently cross the blood retinal barrier. None of these compounds have the requisite characteristics to efficiently improve ocular blood flow. Thus there is a need to identify superior agents to improve blood flow to the back of the eye.

The effect of brinzolamide on regional microvascular ocular blood flow of the cat and rabbit was evaluated using the laser Doppler flowmetry (LDF) and colored microsphere techniques as shown in Examples 1–3. Example 4 describes the tissue distribution of brinzolamide in the eyes of rabbits.

EXAMPLE 1

In a topical study, four cats were bilaterally treated twice a day with one drop of 1% brinzolamide and three cats with one drop of vehicle for one-week. Optic nerve head (ONH) blood flow was then measured by LDF in the anesthetized, spontaneously breathing felines. The experiment was repeated after a one-week interval in the same cats to assess the reproducibility of the technique. Averaging the two blood flow measurements showed that ONH flow was increased by an average of 21.8% over that measured in the control group. In anesthetized, ventilated cats, ONH blood flow was increased on average 16.5%±8% at 60 minutes following a single topical dose. Intravenous brinzolamide produced a 46±17% increase ($p \leq 0.05$) in ONH blood flow; ONH vascular resistance, a measure of vascular tone in the ONH microcirculation, was reduced by 35±8% ($p \leq 0.05$).

EXAMPLE 2

Intravenous administration of 0.5, 2.5, and 5 mg/kg of brinzolamide to anesthetized, ventilated New Zealand albino rabbits produced a significant dose-related increase in total ocular blood which reflected increases in blood flow to the tissues of the eye measured by the colored microsphere technique. Optic nerve head blood flow, measured by LDF, was also increased above baseline. Ocular vascular tone was reduced since total ocular vascular resistance was decreased dose-dependently. In this experiment, it was also possible to compare blood flows of the normal eye to the contralateral eye that was mildly hypofused due to unilateral carotid occlusion. Baseline blood flow was 657±36 µl/min in the hypofused eye. Intravenous doses of brinzolamide produced similar increases in total ocular blood flows of 29%, 68%, and 90% in normal eyes and increases of 21%, 64%, and 90% in hypofused eyes. The highest intravenous brinzolamide dose returned regional blood flows to the hypofused eye to baseline levels found in the normal eye. Percentage wise, the blood flow increase to the hypofused eye was greatest to iridial, ciliary, and choroidal tissues, respectively.

EXAMPLE 3

Topical ocular administration of brinzolamide 2% suspension, one drop twice daily, in a one-week multidose crossover study in nine acepromazine tranquilized Dutch-belted rabbits significantly increased blood flow to the optic nerve head as measured by LDF. Baseline values for optic nerve head (ONH) blood flow, blood pressure, heart rate, intraocular pressure (IOP), and acid-base balance were determined before treatment began and 7–14 days after completion of a treatment arm; baseline values for the measured variables did not significantly change during the experiment. Treatment measurements were made 90 minutes after the last dose on day eight. Optic nerve head blood flow and measured systemic variables were not changed by vehicle treatment. Minimal disturbance of acid-base balance occurred in brinzolamide treated animals. IOP was decreased by 16.8±2.2% ($p<0.05$ versus vehicle; $p<0.001$ versus baseline) and ONH blood flow was significantly increased by 11.2±1.6% (mean±SEM; $p<0.05$) following topical brinzolamide. It is established that the vasculature of the ONH responds to increases in arterial $O_2$ or $CO_2$ tension by a reduction or an enhancement of ONH blood flow, respectively. Since the blood flow increase in this experiment occurred when arterial $CO_2$ tension was below and $O_2$ tension was above baseline levels, it can be suggested that brinzolamide has a local ocular action on the optic nerve head vasculature independent of effects on blood gases.

EXAMPLE 4

The tissue distribution of brinzolamide was determined in New Zealand Albino (NZW) and Dutch belted rabbits after a single topical ocular dose of 1% $^{14}$C-brinzolamide. In both species brinzolamide was found to slowly redistribute into the retina. The $T_{max}$ values in the retina were 20 days and 36 days in the NZW and Dutch belted rabbits respectively. These data demonstrate that brinzolamide is slowly delivered to the retina over time and likely comes for the red blood cells. The $C_{max}$ values were 0.330 and 0.338 ?g equivalents/g in the NZW and Dutch belted rabbits respectively. These data show that the drug distribution is not influenced by the presence/absence of pigment and is not simply a measure of red blood cell concentration.

Brinzolamide is preferably formulated as a topical ophthalmic suspension with a pH of about 4.5–7.8. It will normally be contained in the formulation at a concentration of 0.1%–10% by weight, preferably 0.25%–5.0% by weight. Thus, for topical presentation 1–3 drops of these formulations would be delivered to the surface of the eye 1–4 times a day according to the routine discretion of a skilled clinician.

Brimonidine is preferably formulated as a topical ophthalmic solution with a pH of about 4.5–7.8. It will normally be contained in the formulation at a concentration of 0.01%–0.2% by weight, preferably 0.1%–0.2% by weight. Thus, for topical presentation 1–3 drops of these formulations would be delivered to the surface of the eye 1–4 times a day according to the routine discretion of a skilled clinician.

The combinations of brinzolamide and brimonidine are preferably formulated as topical ophthalmic suspensions with a pH of about 6.5 to 7.8. Brinzolamide will is normally be contained in the formulations at concentrations of 1.0%–2.0% by weight, preferably 1.0% by weight. Brimonidine will normally be contained in the formulations at concentrations of 0.01%–0.2% by weight, preferably 0.05%–0.2% by weight. For these formulations 1–2 drops would be delivered to the surface of the eye 1–3 times a day according to the routine discretion of a skilled clinician.

The following example is the preferred brinzolamide formulation for use according to the present invention.

EXAMPLE 5

| Ingredient | Percent w/v |
| --- | --- |
| Brinzolamide | 1.0 |
| Mannitol | 3.3 |
| Carbopol 974P | 0.4 |
| Tyloxapol | 0.025 |
| Disodium EDTA | 0.01 |
| Benzalkonium Chloride | 0.01 + 5% excess |
| Sodium Chloride | 0.25 |
| Sodium Hydroxide/Hydrochloric Acid | pH 7.5 |
| Purified Water | QS 100 |

EXAMPLE 6

| Ingredient | Percent w/v |
| --- | --- |
| Brinzolamide | 1.0 |
| Brimonidine Tartrate | 0.1 |
| Mannitol | 3.3 |
| Carbopol 974P | 0.4 |
| Tyloxapol | 0.025 |
| Disodium EDTA | 0.01 |
| Benzalkonium Chloride | 0.01 + 5% excess |
| Sodium Chloride | 0.25 |
| Sodium Hydroxide/Hydrochloric Acid | pH 7.5 |
| Purified Water | QS 100 |

EXAMPLE 7

| Ingredient | Percent w/v |
| --- | --- |
| Brinzolamide | 1.0 |
| Brimonidine Tartrate | 0.05 |
| Mannitol | 3.3 |
| Carbopol 974P | 0.4 |
| Tyloxapol | 0.025 |
| Disodium EDTA | 0.01 |
| Benzalkonium Chloride | 0.01 + 5% excess |
| Sodium Chloride | 0.25 |
| Sodium Hydroxide/Hydrochloric Acid | pH 6.5 |
| Purified Water | QS 100 |

EXAMPLE 8

| Ingredient | Percent w/v |
| --- | --- |
| Brinzolamide | 1.0 |
| Brimonidine Tartrate | 0.2 |
| Mannitol | 3.3 |
| Carbopol 974P | 0.4 |
| Tyloxapol | 0.025 |
| Disodium EDTA | 0.01 |
| Benzalkonium Chloride | 0.01 + 5% excess |
| Sodium Chloride | 0.25 |
| Sodium Hydroxide/Hydrochloric Acid | pH 7.5 |
| Purified Water | QS 100 |

EXAMPLE 9

| Ingredient | Percent w/v |
| --- | --- |
| Brinzolamide | 1.0 |
| Brimonidine Tartrate | 0.02 |
| Mannitol | 3.3 |
| Carbopol 974P | 0.4 |
| Tyloxapol | 0.025 |
| Disodium EDTA | 0.01 |
| Benzalkonium Chloride | 0.01 + 5% excess |
| Sodium Chloride | 0.25 |
| Sodium Hydroxide/Hydrochloric Acid | pH 6.5 |
| Purified Water | QS 100 |

EXAMPLE 10

| Ingredient | Percent w/v |
| --- | --- |
| Brimonidine Tartrate | 0.2 |
| Polyvinyl Alcohol | 1.4 |

-continued

| Ingredient | Percent w/v |
|---|---|
| Benzalkonium Chloride | 0.005% |
| Citric Acid | 0.042 |
| Sodium Citrate | 0.53 |
| Sodium Chloride | 0.69 |
| Sodium Hydroxide/Hydrochloric Acid | QS pH 6.3–6.5 |
| Purified Water | QS 100 |

We claim:

1. A method for treating glaucoma which comprises administering a pharmaceutically effective amount of brinzolamide and brimonidine.

2. The method of claim 1 wherein the brinzolamide and the brimonidine are dosed simultaneously in a single formulation.

* * * * *

UNITED STATES PATENT AND TRADEMARK OFFICE
CERTIFICATE OF CORRECTION

PATENT NO.    : 6,316,441 B1
DATED         : November 13, 2001
INVENTOR(S)   : Thomas R. Dean, Louis DeSantis, Jr. and Billie M. York It is certified that error appears in the above-identified patent and that said Letters Patent is hereby corrected as shown below:

<u>Title page,</u>
Item [22], PCT Filed, "April 11, 2001" should read -- December 7, 1999 --.
Item [86], should read -- PCT No.:     PCT/US99/28987
                          § 371 Date:   Aug 4, 2000
                          § 102 (e) Date: Aug 4, 2000 --.
Item [87], should read -- PCT Pub. No.: WO 2004/073708
                          PCT Pub. Date: Sept. 2, 2004 --.
Item [60], Related U.S. Application Data, "Provisional application No. 60/112,750, filed on Dec. 17, 1995", should read -- Provisional application No. 60/112,750, filed on December 17, 1998 --.

Signed and Sealed this

Sixteenth Day of May, 2006

JON W. DUDAS
*Director of the United States Patent and Trademark Office*